US00PP27801P2

(12) United States Plant Patent
Flore

(10) Patent No.: US PP27,801 P2
(45) Date of Patent: Mar. 21, 2017

(54) ***PHALAENOPSIS* PLANT NAMED 'MI00316'**

(50) Latin Name: *Phalaenopsis hybrida*
Varietal Denomination: MI00316

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 14/756,886

(22) Filed: Oct. 26, 2015

(51) Int. Cl.
*A01H 5/02* (2006.01)

(52) U.S. Cl.
USPC ..... Plt./311

(58) Field of Classification Search
USPC ..... Plt./311
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phalaenopsis* plant named 'MI00316', characterized by its upright plant habit; moderately vigorous growth habit; strong flowering stems; freely flowering habit; typically three racemes per plant; each inflorescence with numerous flowers; showy purple to purple violet-colored flowers with fine dots and netting (venation) pattern; and ease of production.

2 Drawing Sheets

Botanical designation: *Phalaenopsis hybrida.*
Cultivar denomination: 'MI00316'.

BACKGROUND OF THE INVENTION

The present invention relates to a new and distinct cultivar of *Phalaenopsis* plant, botanically known as *Phalaenopsis hybrida*, and hereinafter referred to by the name 'MI00316'.

The new *Phalaenopsis* plant is a product of a planned breeding program conducted by the Inventor in Lochristi, Belgium. The objective of the breeding program is to develop new freely flowering *Phalaenopsis* plants with unique and attractive flower patterns and coloration.

The new *Phalaenopsis* plant originated from a cross-pollination in July, 2006 in Lochristi, Belgium of a proprietary selection of *Phalaenopsis hybrida* identified as code number PHM00008, not patented, as the female, or seed, parent with *Phalaenopsis* sp. 'Atlantis', disclosed in U.S. Plant Pat. No. 17,270, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in July, 2009.

Asexual reproduction of the new *Phalaenopsis* plant by in vitro propagation (tissue culture) in a controlled environment in Lochristi, Belgium since March, 2011 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00316'. These characteristics in combination distinguish 'MI00316' as a new and distinct *Phalaenopsis* plant:

1. Upright plant habit.
2. Moderately vigorous growth habit.
3. Strong flowering stems.
4. Freely flowering habit; typically three racemes per plant; each inflorescence with numerous flowers.
5. Showy purple to purple violet-colored flowers with fine dots and netting (venation) pattern.
6. Ease of production.

Plants of the new *Phalaenopsis* can be compared to plants of the female parent selection. Plants of the new *Phalaenopsis* differ primarily from plants of the female parent selection in leaf orientation and size as plants of the new *Phalaenopsis* have shorter and more upright leaves than plants of the female parent selection.

Plants of the new *Phalaenopsis* can be compared to plants of the male parent, 'Atlantis'. Plants of the new *Phalaenopsis* differ primarily from plants of 'Atlantis' in flower color as plants of 'Atlantis' do not have a prominent netting (venation) pattern. In addition, plants of the new *Phalaenopsis* have a faster growth rate than plants of 'Atlantis'.

Plants of the new *Phalaenopsis* can be compared to plants of *Phalaenopsis hybrida* 'Kansas City', not patented. In side-by-side comparisons conducted in Lochristi, Belgium, plants of the new *Phalaenopsis* differ primarily from plants of 'Kansas City' in flowering habit as plants of the new *Phalaenopsis* typically produce more inflorescences per plant. Additionally, plants of the new *Phalaenopsis* have slightly smaller flowers than plants of 'Kansas City'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00316' grown in a container.

The photograph on the second sheet is a close-up view of typical flowers of 'MI00316'.

DETAILED BOTANICAL DESCRIPTION

The aforementioned photographs and following observations and measurements describe plants grown during the summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/$m^2$ to 375 Watt/$m^2$. Plants were exposed to eight weeks of cooling to induce flowering. Plants were 78 weeks from propagation when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00316'.

Parentage:

- *Female parent*.—Proprietary selection of *Phalaenopsis hybrida* identified as code number PHM00008, not patented.
- *Male parent*.—*Phalaenopsis* sp. 'Atlantis', disclosed in U.S. Plant Pat. No. 17,270.

Propagation:

- *Type*.—By in vitro propagation (tissue culture).
- *Time to initiate roots, summer*.—About nine to ten weeks at temperatures about 26° C.
- *Time to initiate roots, winter*.—About ten to eleven weeks at temperatures about 26° C.
- *Time to produce a rooted young plant, summer*.—About 140 to 160 weeks at temperatures about 26° C.
- *Time to produce a rooted young plant, winter*.—About 150 to 180 weeks at temperatures about 26° C.
- *Root description*.—Thick, fleshy; typically grey green in color, towards the apex, close to light green occasionally with a purple-colored blush.
- *Rooting habit*.—Non-branching; sparse.

Plant description:

- *Plant form and growth habit*.—Herbaceous epiphyte; upright plant habit with typically three panicles or racemes per plant, each inflorescence with numerous flowers; monopodial; moderately vigorous growth habit and moderate growth rate; easy to produce.
- *Plant height, substrate level to top of foliar plane*.—About 17 cm.
- *Plant height, substrate level to top of inflorescences*.—About 42.4 cm.
- *Plant diameter or spread*.—About 36 cm.

Leaf description:

- *Arrangement*.—Distichous, simple; sessile.
- *Length*.—About 16.5 cm.
- *Width*.—About 6 cm.
- *Aspect*.—Somewhat upright to horizontal.
- *Shape*.—Narrowly obovate to elliptic.
- *Apex*.—Acute, unequal.
- *Base*.—Sheathing.
- *Margin*.—Entire; slightly revolute.
- *Texture, upper and lower surfaces*.—Slightly furrowed; glabrous; durable.
- *Luster, upper and lower surfaces*.—Moderately glossy.
- *Venation pattern*.—Camptodromous.
- *Color*.—Developing leaves, upper surface: Close to N137B. Developing leaves, lower surface: Close to 146A to 146B. Fully expanded leaves, upper surface: Close to between 137A and 146A; venation, close to between 137A and 146A. Fully expanded leaves, lower surface: Close to 146B; venation, close to 146A.

Inflorescence description:

- *Appearance and flowering habit*.—Showy zygomorphic flowers arranged on axillary racemes; typically three racemes per plant; each inflorescence with about seven flowers; flowers face outwardly on arching inflorescences supported by strong upright peduncles; flowers with three petals, one petal transformed into a labellum and three sepals.
- *Fragrance*.—None detected.
- *Time to flower*.—Plants begin flowering about 18 weeks after an inductive cooling period.
- *Flower longevity*.—Individual flowers maintain good substance for about four months on the plant; flowers not persistent.
- *Inflorescence length* (*lowermost flower to inflorescence apex*).—About 16.7 cm.
- *Inflorescence width*.—About 14.5 cm to 14.7 cm.
- *Flower buds*.—Height: About 6 mm. Diameter: About 5 mm. Shape: Ovoid. Color: Close to between 70B and 77B.
- *Flower diameter*.—About 7.8 cm.
- *Flower depth*.—About 3 cm.
- *Petals, quantity and arrangement*.—Three, two lateral petals and one lower petal transformed into a labellum.
- *Lateral petals*.—Length: About 3.5 cm. Width: About 4.2 cm. Shape: Reniform. Apex: Rounded. Margin: Entire. Texture, upper and lower surfaces: Glabrous; velvety. Luster, upper and lower surfaces: Matte. Color: When opening, upper surface: Close to between NN78A and N80A; towards the margins, close to N80B; towards the base, close to 77C to 77D; fine dots, close to between NN78A and N80A; venation, closer to N78A. When opening, lower surface: Close to 77B to 77C; venation, close to N78B. Fully opened, upper surface: Close to between NN78B and N80A; towards the margins, close to N80B; towards the base, close to 77D; fine dots, close to between NN78B and N80A; venation, closer to N78A. Fully opened, lower surface: Close to 77C; venation, close to N78B.
- *Labellum*.—Length: About 2.6 cm. Width: About 2.3 cm. Shape: Tri-lobed; two lateral lobes, ovate; central lobe, hastate. Apex: Lateral lobes, obtuse; central lobe, cleft with two long narrow recurved tips. Callosities: Located at the base of the labellum and attachment point of the lateral petals; about 4 mm in length, about 5.5 mm in width and about 6 mm in height. Margin: Entire. Texture, upper and lower surfaces: Glabrous; moderately velvety. Luster, upper and lower surfaces: Matte. Color: When opening, upper surface: Lateral lobes: Close to 71A; towards the apex, close to N78A; towards the base, close to 76C and tinged with close to 12B; marbled and striped with close to 71A and 71B. Central lobe: Close to 72A; towards the margins, close to 71A. Callosities: Close to 15B; fine dots, close to 59A to 59B. When opening, lower surface: Lateral lobes: Close to N78A; towards the base, close to N79C; towards the apex, close to 76C. Central lobe: Close to N78B; tips and margins, close to 72A. Fully opened, upper surface: Lateral lobes: Close to 71A; towards the apex, close to N78B; towards the base, close to 76D and tinged with close to 12B; marbled and striped with close to 71A and 71B. Central lobe: Close to N78A. Callosities: Close to 15B to 15C; fine dots, close to 59A to 59B. Fully opened, lower surface: Lateral lobes: Close to N78A; towards the base, close to N79C; towards the apex, close to 76C. Central lobe: Close to N78B; tips and margins, close to 72A.

*Sepals, quantity and arrangement*.—Three, two lower lateral sepals and one upper dorsal sepal.

*Lateral sepals*.—Length: About 3.7 cm. Width: About 2.5 cm. Shape: Ovate. Apex: Obtuse to broadly and bluntly acute. Base: Obtuse to truncate. Margin: Entire. Texture, upper and lower surfaces: Glabrous; velvety. Luster, upper and lower surfaces: Matte. Color: When opening and fully opened, upper surface: Close to between N78A and NN78A; towards the base, close to between N78B and NN78B; venation, close to N78A. When opening and fully opened, lower surface: Close to N78C; towards the apex, close to N78B.

*Dorsal sepal*.—Length: About 3.6 cm. Width: About 2.8 cm. Shape: Ovate to broadly ovate. Apex: Obtuse. Base: Obtuse to truncate. Margin: Entire. Texture, upper and lower surfaces: Glabrous; velvety. Luster, upper and lower surfaces: Matte. Color: When opening and fully opened, upper surface: Close to between N78A and NN78A; towards the base, close to between N78B and NN78B; venation, close to N78A. When opening and fully opened, lower surface: Close to N78C; towards the apex, close to N78B.

*Peduncles*.—Length: About 43.1 cm. Diameter: About 5 mm. Strength: Strong. Aspect: Upright to about 45° from vertical. Texture: Smooth, glabrous. Luster: Matte. Color: Close to 200A heavily dotted with close to 147D.

*Pedicels*.—Length: About 4.1 cm. Diameter: About 3 mm. Strength: Moderately strong. Aspect: About 70° from peduncle axis. Texture: Smooth, glabrous. Luster: Matte. Color: Close to 76B; proximally, tinged with close to 177B; distally, close to N75C to N75D.

*Reproductive organs*.—Androecium: Column length: About 8 mm. Column width: About 5.5 mm. Column color: Close to between N78B and NN78B. Pollinia quantity: Two. Pollinia diameter (per two pollinia): About 2 mm. Pollinia color: Close to 21A. Gynoecium: Stigma length: About 3 mm. Stigma width: About 4 mm. Stigma shape: Reniform. Stigma color: Close to N155A. Ovary length: About 8 mm. Ovary diameter: About 3 mm. Ovary color: Close to N75C to N75D. Seeds and fruits: Seed and fruit development have not been observed on plants of the new *Phalaenopsis*.

Disease & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00316' as illustrated and described.

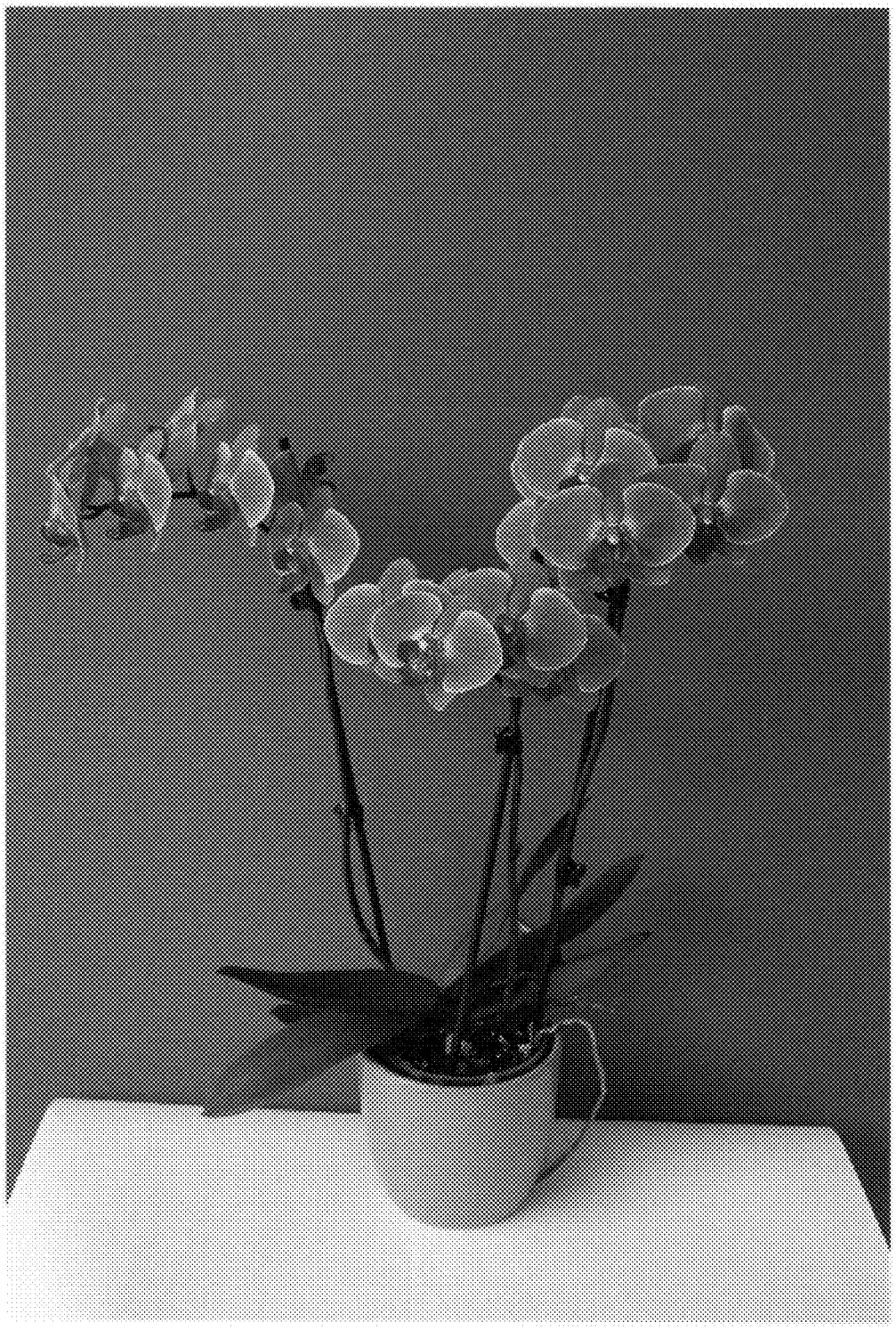

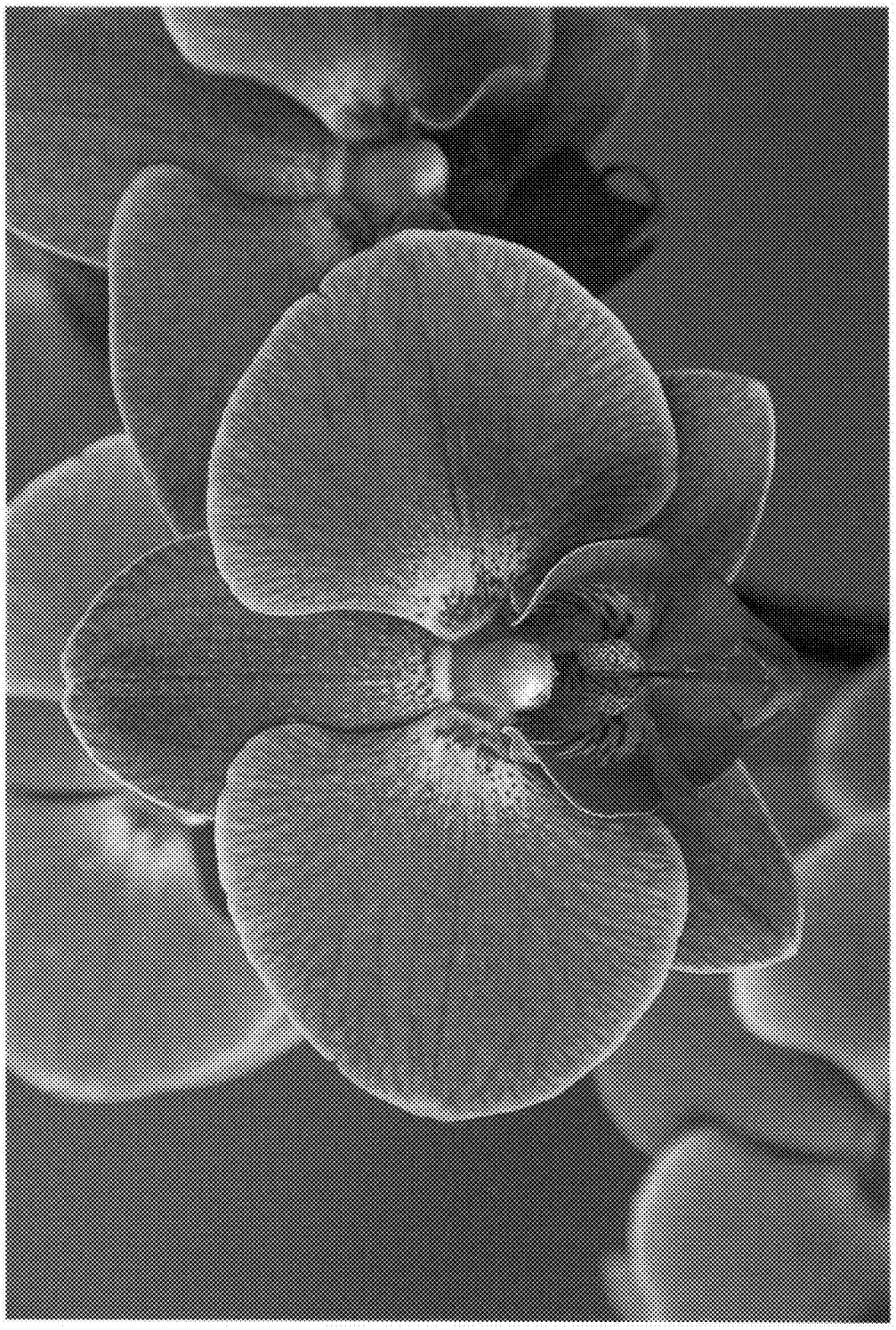

* * * * *